United States Patent
Escobar et al.

(10) Patent No.: US 9,055,933 B2
(45) Date of Patent: Jun. 16, 2015

(54) LARGE BORE CLOSURE SECONDARY HEMOSTASIS BIOADHESIVE DELIVERY SYSTEMS AND METHODS

(71) Applicant: ST. JUDE MEDICAL PUERTO RICO LLC, Caguas, PR (US)

(72) Inventors: Martha Escobar, Jordan, MN (US); Scott Kramer, Minneapolis, MN (US); Edward E. Parsonage, St. Paul, MN (US); Scott Smith, Monticello, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 245 days.

(21) Appl. No.: 13/797,302

(22) Filed: Mar. 12, 2013

(65) Prior Publication Data

US 2014/0276974 A1    Sep. 18, 2014

(51) Int. Cl.
*A61B 17/04*       (2006.01)
*A61B 17/00*       (2006.01)
*A61B 17/06*       (2006.01)

(52) U.S. Cl.
CPC ......... *A61B 17/0057* (2013.01); *A61B 17/0469* (2013.01); *A61B 17/0482* (2013.01); *A61B 2017/00495* (2013.01); *A61B 2017/0065* (2013.01); *A61B 2017/00663* (2013.01); *A61B 2017/0472* (2013.01); *A61B 2017/06042* (2013.01)

(58) Field of Classification Search
CPC .............. A61B 17/0057; A61B 2017/00646; A61B 2017/00663; A61B 2017/00654; A61B 2017/0065; A61B 17/0469; A61B 17/0482; A61B 17/06004; A61B 2017/06042; A61B 17/00491; A61B 2017/00495
See application file for complete search history.

(56) References Cited

U.S. PATENT DOCUMENTS

| | | | |
|---|---|---|---|
| 3,470,875 A | 10/1969 | Johnson | |
| 4,890,612 A * | 1/1990 | Kensey | ........................ 606/213 |
| 5,431,666 A | 7/1995 | Sauer et al. | |
| 5,520,702 A | 5/1996 | Sauer et al. | |
| 5,562,686 A | 10/1996 | Sauer et al. | |
| 5,613,974 A | 3/1997 | Andreas et al. | |
| 5,643,292 A | 7/1997 | Hart | |

(Continued)

FOREIGN PATENT DOCUMENTS

| | | |
|---|---|---|
| EP | 0818178 A2 | 1/1998 |
| EP | 1158907 A1 | 12/2001 |

(Continued)

OTHER PUBLICATIONS

PCT Communication Relating to the Results of the Partial International Search for International Application No. PCT/US2012/041196, mailed Sep. 11, 2012.

(Continued)

*Primary Examiner* — Jonathan W Miles
(74) *Attorney, Agent, or Firm* — Holland & Hart

(57) ABSTRACT

A vascular closure assembly includes a suture placement device and a sealant delivery device. The suture placement device is operable to position at least one suture across the puncture to form a primary seal of the puncture. The sealant delivery device includes a sealant delivery tube having a first lumen sized to receive the at least one suture, and a second lumen configured to deliver a volume of sealant to the puncture after forming the primary seal to create a secondary seal of the puncture. The sealant delivery device is slidable along the at least one suture to the puncture.

20 Claims, 11 Drawing Sheets

(56) References Cited

U.S. PATENT DOCUMENTS

| | | |
|---|---|---|
| 5,674,231 A | 10/1997 | Green et al. |
| 5,700,273 A | 12/1997 | Buelna et al. |
| 5,709,692 A | 1/1998 | Mollenauer et al. |
| 5,728,114 A | 3/1998 | Evans et al. |
| 5,766,183 A | 6/1998 | Sauer |
| 5,810,851 A | 9/1998 | Yoon |
| 5,860,990 A | 1/1999 | Nobles et al. |
| 5,972,005 A | 10/1999 | Stalker et al. |
| 6,036,699 A | 3/2000 | Andreas et al. |
| 6,048,357 A | 4/2000 | Kontos |
| 6,059,800 A | 5/2000 | Hart et al. |
| 6,136,010 A | 10/2000 | Modesitt et al. |
| 6,355,050 B1 | 3/2002 | Andreas et al. |
| 6,562,052 B2 | 5/2003 | Nobles et al. |
| 6,623,509 B2 | 9/2003 | Ginn |
| 6,641,592 B1 | 11/2003 | Sauer et al. |
| 6,896,692 B2 | 5/2005 | Ginn et al. |
| 6,911,034 B2 | 6/2005 | Nobles et al. |
| 6,932,824 B1 | 8/2005 | Roop et al. |
| 6,964,668 B2 | 11/2005 | Modesitt et al. |
| 6,969,397 B2 | 11/2005 | Ginn |
| 7,001,400 B1 | 2/2006 | Modesitt et al. |
| 7,083,635 B2 | 8/2006 | Ginn |
| 7,235,087 B2 | 6/2007 | Modesitt et al. |
| 7,361,183 B2 | 4/2008 | Ginn |
| 7,390,328 B2 | 6/2008 | Modesitt |
| 7,553,319 B2 | 6/2009 | Bagaoisan et al. |
| 7,601,161 B1 | 10/2009 | Nobles et al. |
| 7,621,937 B2 | 11/2009 | Pipenhagen et al. |
| 7,686,821 B2 | 3/2010 | Hathaway et al. |
| 7,731,726 B2 | 6/2010 | Belhe et al. |
| 7,744,610 B2 | 6/2010 | Hausen |
| 7,752,853 B2 | 7/2010 | Singh et al. |
| 7,753,933 B2 | 7/2010 | Ginn et al. |
| 7,837,696 B2 | 11/2010 | Modesitt et al. |
| 7,842,047 B2 | 11/2010 | Modesitt et al. |
| 7,842,048 B2 | 11/2010 | Ma |
| 7,846,170 B2 | 12/2010 | Modesitt et al. |
| 7,850,701 B2 | 12/2010 | Modesitt et al. |
| 7,883,517 B2 | 2/2011 | Pantages et al. |
| 7,985,240 B2 | 7/2011 | Bagaoisan et al. |
| 8,029,476 B2 | 10/2011 | Rosenberg et al. |
| 8,048,092 B2 | 11/2011 | Modesitt et al. |
| 8,083,768 B2 | 12/2011 | Ginn et al. |
| 8,192,456 B2 | 6/2012 | Holman et al. |
| 8,333,787 B2 | 12/2012 | Pipenhagen et al. |
| 8,506,592 B2 | 8/2013 | Killion et al. |
| 2005/0085854 A1 | 4/2005 | Ginn |
| 2006/0212071 A1 | 9/2006 | Ginn et al. |
| 2008/0065151 A1 | 3/2008 | Ginn |
| 2008/0215088 A1 | 9/2008 | Hnojewyj et al. |
| 2008/0221616 A1 | 9/2008 | Ginn et al. |
| 2009/0054926 A1 | 2/2009 | Pipenhagen et al. |
| 2009/0099578 A1 | 4/2009 | Heneveld et al. |
| 2009/0223426 A1* | 9/2009 | Shonteff et al. ............... 112/169 |
| 2009/0306685 A1 | 12/2009 | Fill |
| 2010/0042118 A1 | 2/2010 | Garrison et al. |
| 2010/0185216 A1 | 7/2010 | Garrison et al. |
| 2011/0071567 A1 | 3/2011 | Modesitt et al. |
| 2011/0166595 A1 | 7/2011 | Vidlund et al. |
| 2011/0282383 A1 | 11/2011 | Vidlund et al. |
| 2013/0006299 A1 | 1/2013 | Pipenhagen et al. |
| 2013/0144316 A1 | 6/2013 | McCrea et al. |
| 2013/0190808 A1 | 7/2013 | Tegels et al. |
| 2013/0190812 A1 | 7/2013 | Vidlund |
| 2013/0190813 A1 | 7/2013 | Tegels et al. |

FOREIGN PATENT DOCUMENTS

| | | |
|---|---|---|
| EP | 1327419 A2 | 7/2003 |
| EP | 1349501 A2 | 10/2003 |
| EP | 1677682 A2 | 7/2006 |
| EP | 1972282 A2 | 9/2008 |
| EP | 2147640 A2 | 1/2010 |
| EP | 2298180 A1 | 3/2011 |
| WO | 9703613 A1 | 2/1997 |
| WO | 0051498 | 9/2000 |
| WO | 0078226 A1 | 12/2000 |
| WO | 2010081106 A1 | 7/2010 |

OTHER PUBLICATIONS

U.S. Appl. No. 13/770,586, filed Feb. 19, 2013.
U.S. Appl. No. 13/770,714, filed Feb. 19, 2013.
U.S. Appl. No. 13/772,834, filed Feb. 21, 2013.
U.S. Appl. No. 13/773,062, filed Feb. 21, 2013.
U.S. Appl. No. 13/773,206, filed Feb. 21, 2013.
U.S. Appl. No. 13/778,408, filed Feb. 27, 2013.
U.S. Appl. No. 13/778,529, filed Feb. 27, 2013.
U.S. Appl. No. 13/778,701, filed Feb. 27, 2013.
U.S. Appl. No. 13/778,798, filed Feb. 27, 2013.
U.S. Appl. No. 13/778,624, filed Feb. 27, 2013.
U.S. Appl. No. 13/779,031, filed Feb. 27, 2013.
Notification of Transmittal of the International Search Report and the Written Opinion of the International Searching Authority, or the Declaration for International Application No. PCT/US2012/064768, mailed Feb. 19, 2013, (18 pp.).
Notification of Transmittal of the International Search Report and the Written Opinion of the International Searching Authority, or the Declaration for International Application No. PCT/US2012/066012, mailed Feb. 19, 2013, (17 pp.).
Notification of Transmittal of the International Search Report and the Written Opinion of the International Searching Authority, or the Declaration for International Application No. PCT/US2012/064770, mailed Feb. 19, 2013, (16 pp.).
PCT International Search Report for International Application No. PCT/US2014/019808 mailed May 28, 2014 (2 pp.).

* cited by examiner

LARGE BORE CLOSURE SECONDARY HEMOSTASIS BIOADHESIVE DELIVERY SYSTEMS AND METHODS

TECHNICAL FIELD

The present disclosure relates generally to methods and systems for sealing tissue punctures, and more particularly, to methods and systems for sealing large bore openings in vessels using multiple closure mechanisms.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture.

Closing large bore openings in a vessel may be particularly difficult using a pre-formed or flowable sealing material on an exterior surface of the vessel. Challenges exist related to holding closed a large bore opening using only a sealing material because of the large size of the opening and the natural forces tending to bias the opening away from a closed position. Opportunities exist for improvement in closing large bore openings to improve hemostasis.

SUMMARY

One aspect of the present disclosure relates to a vascular closure assembly configured to seal an opening or puncture in a vessel. The vascular closure assembly includes a suture placement device and a sealant delivery device. The suture placement device is operable to position at least one suture across the puncture to form a primary seal of the puncture. The sealant delivery device includes a sealant delivery tube having a first lumen sized to receive the at least one suture, and a second lumen configured to deliver a volume of sealant to the puncture after forming the primary seal to create a secondary seal of the puncture. The sealant delivery device is slidable along the at least one suture to the puncture.

The sealant delivery tube may include a suture insertion slot at a distal end of the sealant delivery tube. The sealant delivery tube may include a helical shaped suture insertion slot at a distal end thereof, and a longitudinal guide slot open to the helical shaped suture insertion slot. The sealant delivery tube may include a helical shaped suture insertion slot at a distal end thereof, wherein the insertion slot forms an acute angle along its length. The sealant delivery device may include a suture retaining member positioned at a distal end thereof, wherein the suture retaining member permits one-way insertion of the at least one suture into the first lumen. The suture placement device may position the at least one suture on opposite sides of the puncture, and tension may be retained in the at least one suture with one of a knot and a suture locking device to at least partially seal the puncture prior to delivering the volume of sealant.

Another aspect of the present disclosure relates to a method of closing a puncture in a vessel. The method includes providing a suture placement device and a sealant delivery device, positioning at least one suture across the puncture with the suture placement device, sealing the puncture with the at least one suture, advancing the sealant delivery device along the at least one suture to the puncture, and delivering a volume of sealant through the sealant delivery device to the puncture to further seal the puncture.

The method may also include providing a releasable connection between the sealant delivery device and the at least one suture. Delivering a volume of sealant may include mixing the volume of sealant in the sealant delivery device during delivery. The sealant delivery device may include a first lumen configured to receive the at least one suture and a second lumen configured to deliver the volume of sealant. Sealing the puncture may include advancing a knot along the at least one suture to the puncture. The at least one suture may include two suture portions and the sealant delivery device may be advanced along both suture portions to the puncture.

The sealant delivery device may include a sealant shaft and an insertion slot extending proximally from an open distal end of the sealant shaft, and the method may include inserting the at least one suture into the insertion slot prior to advancing the sealant delivery device. The sealant delivery device may include a guide slot spaced proximal of the open distal end and intersecting with the insertion slot, and the method may include inserting the at least one suture through the insertion slot and into the guide slot prior to advancing the sealant delivery device. The method may include inserting the at least one suture into a portion of the sealant delivery device before advancing the sealant delivery device.

Another example method in accordance with the present disclosure relates to sealing a puncture in a vessel accessible through a percutaneous incision. The method includes providing a sealant delivery device having first and second lumens, and a suture placement device, positioning at least one suture across the puncture with the suture placement device, advancing a knot along the at least one suture to seal the puncture, positioning the at least one suture in the first lumen, advancing the sealant delivery device along the at least one suture to the puncture, and delivering a volume of sealant through the second lumen to the puncture to seal the puncture.

The sealant delivery device may include a helical shaped insertion slot providing lateral access into the first lumen, and positioning the at least one suture in the first lumen includes laterally inserting the at least one suture through the insertion slot. The sealant delivery device may include a guide slot intersecting the insertion slot and extending longitudinally, and positioning the at least one suture in the first lumen includes positioning the at least one suture in the guide slot. The sealant may include a resorbable bioadhesive. Positioning at least one suture across the puncture with the suture placement device may include inserting the suture placement device in the puncture, advancing at least one needle through a wall of the vessel adjacent to the puncture, drawing the at least one suture through the wall of the vessel, and removing the suture placement device from the puncture.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

Figure 1:
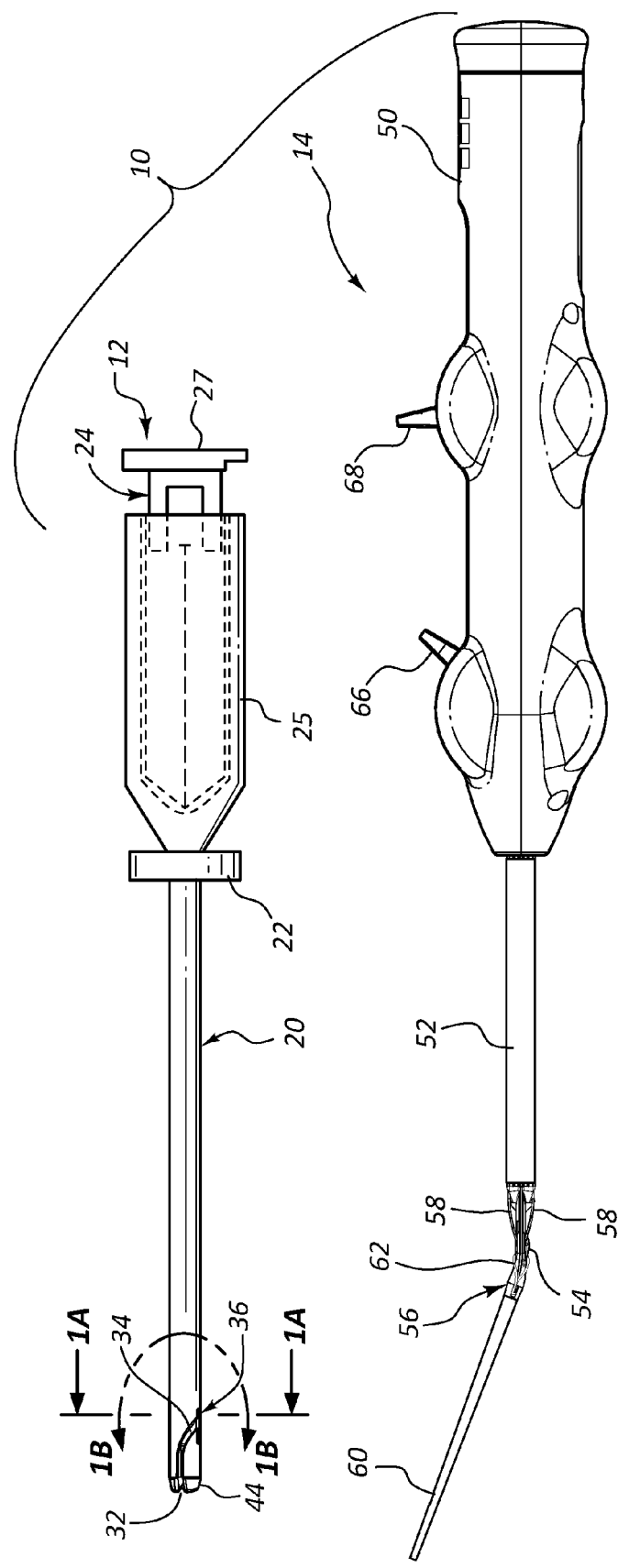
FIG. 1 shows components of an example vascular closure system in accordance with the present disclosure.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

As used in this specification and the appended claims, the terms "engage" and "engagable" are used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

The general structure and function of tissue closure devices used for sealing a tissue puncture in an internal tissue wall accessible through an incision in the skin are known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

An exemplary embodiment of the present disclosure includes a vascular closure system used to provide hemostatis of a vessel puncture. One aspect of the present disclosure relates to systems and methods for achieving secondary hemostatis of a vessel puncture that has been closed using at least one suture. The vascular closure system may include a bioadhesive delivery device configured to apply bioadhesive to a previously sutured vessel puncture (e.g., arteriotomy). The bioadhesive may work in conjunction with the suture to maintain hemostatis. The use of a bioadhesive to achieve hemostatis in combination with a suture closure of the vessel puncture may be particularly useful when dealing with large arteriotomies (e.g., 18 French (F) to 24 F).

The bioadhesive delivery device may include a syringe loaded with a bioadhesive, and a delivery sheath coupled in flow communication with the syringe for delivery of the bioadhesive to the vessel puncture. For the procedure, the vessel puncture may have been pre-sutured using a separate large bore closure device or other suture placement device. The sutures may be secured using, for example, knots or a suture locking device such as a clip. A distal tip of the delivery sheath may be designed to communicate with the protruding suture to help advance the bioadhesive delivery device down a percutaneous tissue tract to the vessel. The bioadhesive may be applied to help secure the suture and further seal the vessel puncture to provide improved hemostasis.

As mentioned above, the vascular closure system may be particularly useful as part of closing a large bore tissue puncture. Large bore tissue punctures are typically in the range from about 5 F to about 30 F, and more particularly from 10 F to about 25 F. A suture placement device may be used to place at least one suture through tissue adjacent to the tissue puncture. In one example, the suture placement device places two sutures in a wall of the vessel adjacent to the vessel puncture. A suture placement device may be operable percutaneously through a layer of tissue (e.g., skin or fat) that provides access via a tissue tract to the vessel puncture.

Suture locking devices or knots may be used to apply and maintain tension in the sutures to at least partially seal the vessel puncture. The free ends of the suture may extend out of the layer of tissue for use in guiding the bioadhesive delivery device to the vessel. The free ends of the suture may be captured by or extend through a portion of the bioadhesive delivery device to provide improved guiding to the vessel puncture. The sealant delivery device may be configured with rapid exchange features that permit mounting the sealant delivery device to the sutures at a location outside of the tissue tract and distal of the proximal ends of the sutures. The free ends of the suture may be cut within the tissue tract after delivery of the bioadhesive and removal of the sealant delivery device.

Referring now to FIG. 1, an example vascular closure system 10 (also referred to as a vascular closure assembly) is shown and described. The vascular closure system 10 includes a sealant delivery device 12 and an optional suture placement device 14. The suture placement device 14 may be used to position at least one suture cross a vessel puncture. The suture placement device 14 is removed and the sealant delivery device 12 is advanced along the suture to the vessel puncture. The sealant delivery device 12 deposits a volume of bioadhesive at the vessel puncture. The suture and bioadhesive may be used to seal the vessel puncture and provide hemostatis. A knot or suture locking device may be advanced along the suture to at least partially seal the vessel puncture prior to delivery of the bioadhesive.

Figure 1A:
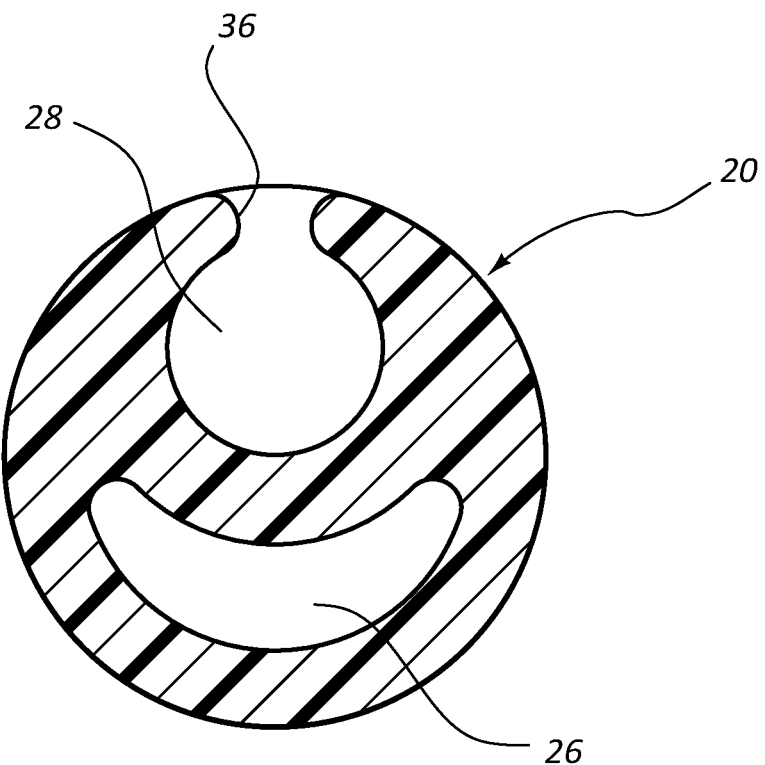
FIG. 1A is a cross-sectional view of a sealant delivery device of the vascular closure system shown in FIG. 1 taken along cross-sectional indicators 1A-1A.
Figure 1B:
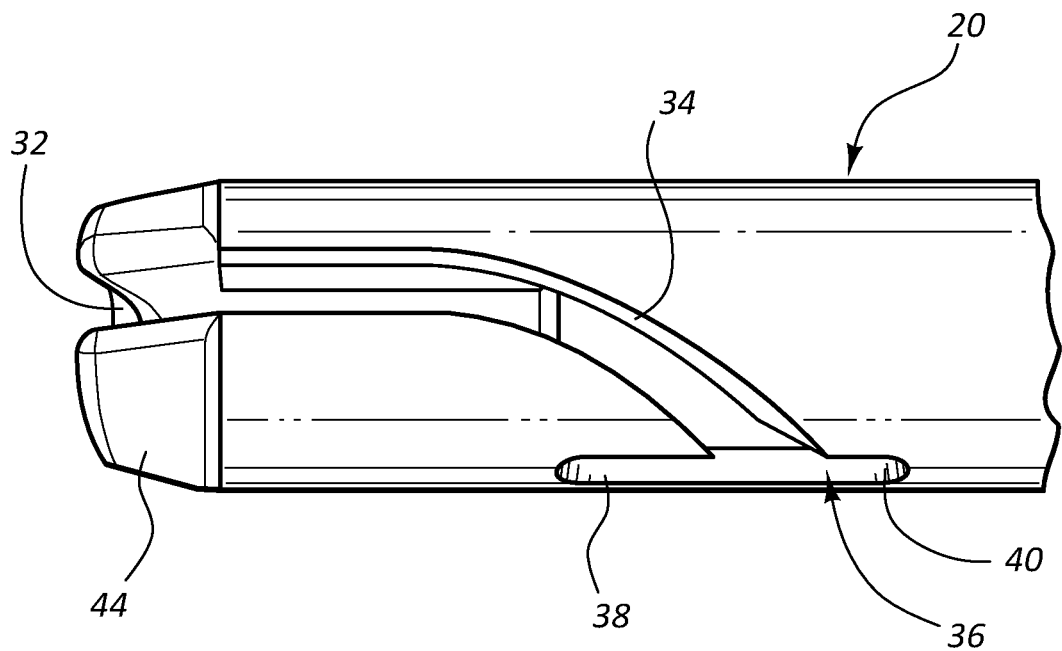
FIG. 1B is a close-up view of a distal end portion of the sealant delivery device of the vascular closure system of FIG. 1.

Referring now to FIGS. 1-1B, the sealant delivery device 12 includes a sealant shaft 20 (also referred to as a delivery sheath), a sealant manifold 22, and a sealant mixing device 24. The sealant shaft 20 includes a sealant lumen 26 (see FIG. 1A) and an exchange lumen 28. The sealant lumen 26 is coupled in flow communication with the sealant mixing device 24 via the sealant manifold 22. The sealant mixing device 24 includes a housing 25 and a plunger 27. Operating the plunger 27 in an axial direction relative to the housing 25 advances the bioadhesive through the sealant manifold 22 and the sealant lumen 26, and out at the vessel puncture.

The exchange lumen 28 includes a distal end opening 32, insertion slot 34, a longitudinal guide slot 36, and a tip 44 (see FIG. 1B). The tip 44 may define at least in part the distal end opening 32 and the insertion slot 34. The insertion slot 34 may have a contoured shape such as a helical shape. The insertion slot 34 may be referred to as a helical insertion slot. Many other shapes and constructions are possible for the insertion slot 34. The insertion slot 34 permits a suture to be threaded into the longitudinal guide slot 36 at any point along a length of the suture. The insertion slot 34 may extend through approximately 90° as shown in FIG. 1B, although the insertion slot 34 may also traverse smaller or larger angles such as 180°. The insertion slot 34 is open to the distal end opening 32 and intersects with the longitudinal guide slot 36.

The longitudinal guide slot 36 may be shaped generally like a capsule with the insertion slot 34 intersecting the longitudinal guide slot 36 at a location spaced between its distal and proximal ends 38, 40. The longitudinal guide slot 36 may have a shape and orientation that limits an inserted suture from falling out of the longitudinal guide slot 36. As a suture, such as the suture 62 shown in FIG. 2A and FIGS. 4-10, is threaded into the insertion slot 34 and longitudinal guide slot 36, the suture tends to fall towards the proximal end 40 of the longitudinal guide slot 36, which prevents the suture 62 from slipping back out of the insertion slot 34. In at least one example, the longitudinal guide slot 36 is aligned parallel with the longitudinal axis of the sealant shaft 20.

Figure 2A:
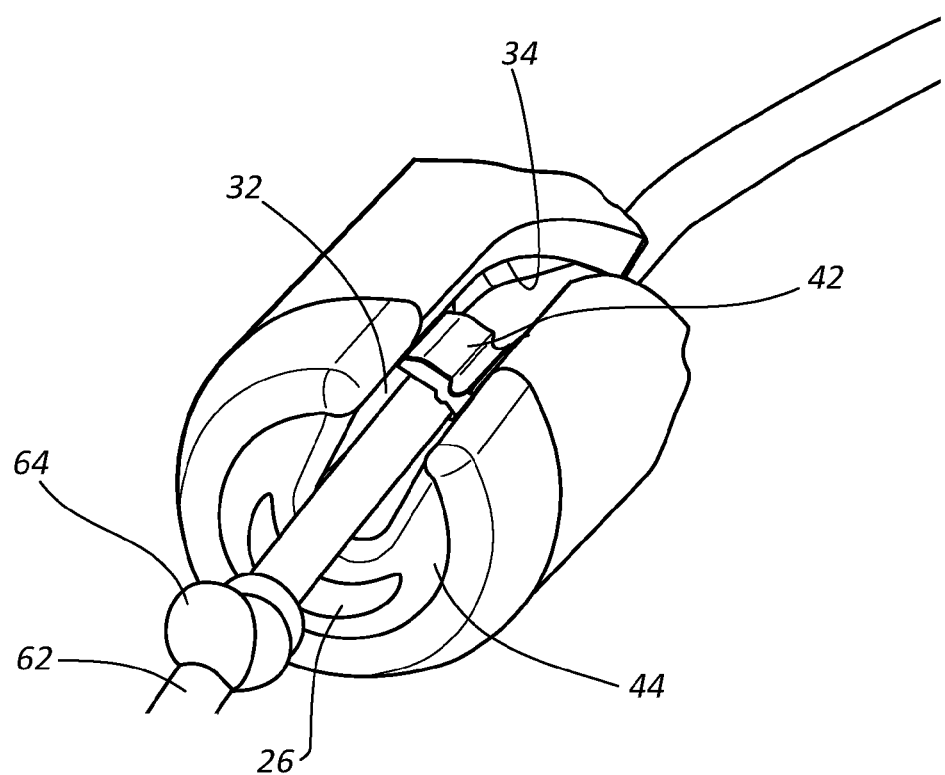
FIG. 2A is a close-up view of a distal end portion of another example sealant delivery device.
Figure 2B:
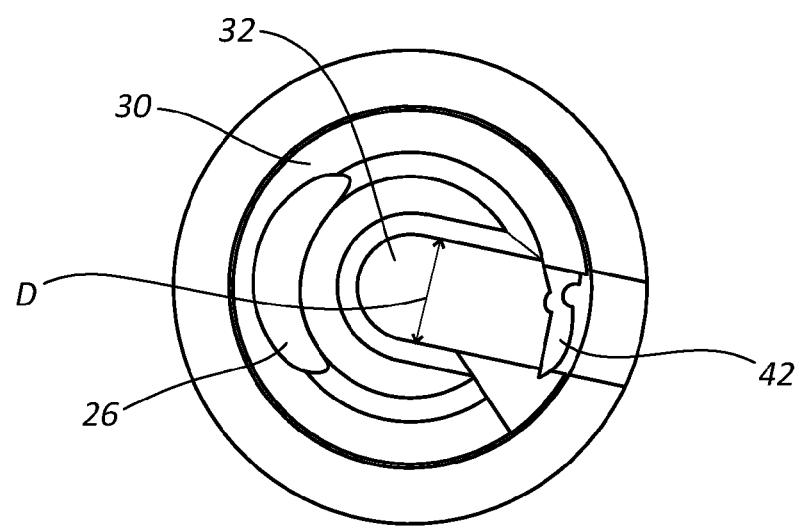
FIG. 2B is an end view of the sealant delivery device of FIG. 2A.

The tip 44 may include various features which assist in advancing the suture 62 into the insertion slot 34. The tip 44 may include tapered features such as a tapered opening at a distal surface thereof or along side surfaces thereof in alignment with the insertion slot 34 to enhance insertion of the suture 62. In one example, the tip 44 includes a cantilever arm 42 (see FIGS. 2A-2B). The cantilever arm may act as a one-way opening or door. The suture 62 may deflect the cantilever arm 42 while moving into the insertion slot 34. The cantilever arm 42 may automatically move back into the position of FIGS. 2A-2B to capture the suture 62 within the exchange lumen 28. The cantilever arm 42 may limit movement of the suture 62 out of the exchange lumen 28 while advancing the sealant delivery device 12 along the suture 62 to the vessel puncture. In one example, the suture 62 may be removed from the exchange lumen 28 only by retracting the sealant delivery device 12 proximately off a distal end of the suture 62 when the cantilever arm 42 or a similar feature is used to capture the suture 62.

The distal end opening 32 into the exchange lumen 28 may have a diameter D (see FIG. 2B), which is large enough to allow a suture to slide freely therethrough. The diameter D may be small enough to prevent any knots tied into the suture (e.g., knot 64 shown in FIG. 2A) or a suture locking device attached to the suture from entering through the tip 44. Consequently, knots such as knot 64 used to hold closed the vessel puncture cannot enter the exchange lumen 28. In some examples, the diameter D may be no more than approximately two to three times the diameter of the suture 62. In one example, the suture has a diameter of about 0.12 mm and the internal diameter D is no more than about 0.35 mm.

Figure 3B:
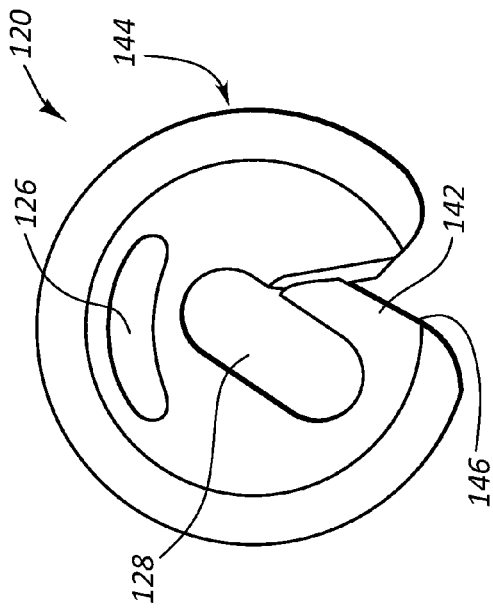
FIG. 3B is an end view of the sealant delivery device of FIG. 3A in a closed position.
Figure 3C:
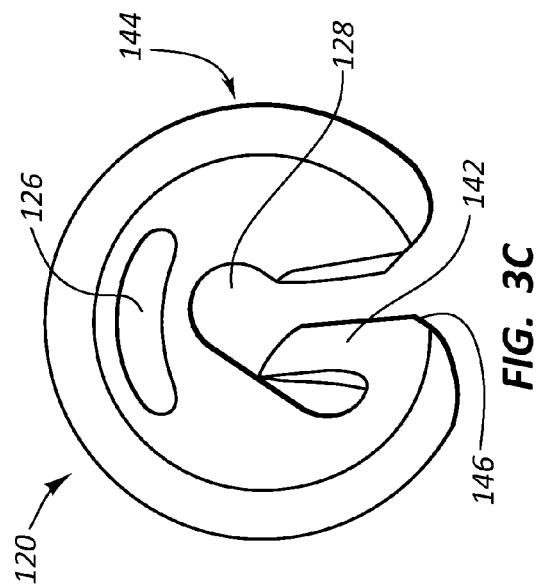
FIG. 3C is an end view of the sealant delivery device of FIG. 3A in an open position.
Figure 3A:
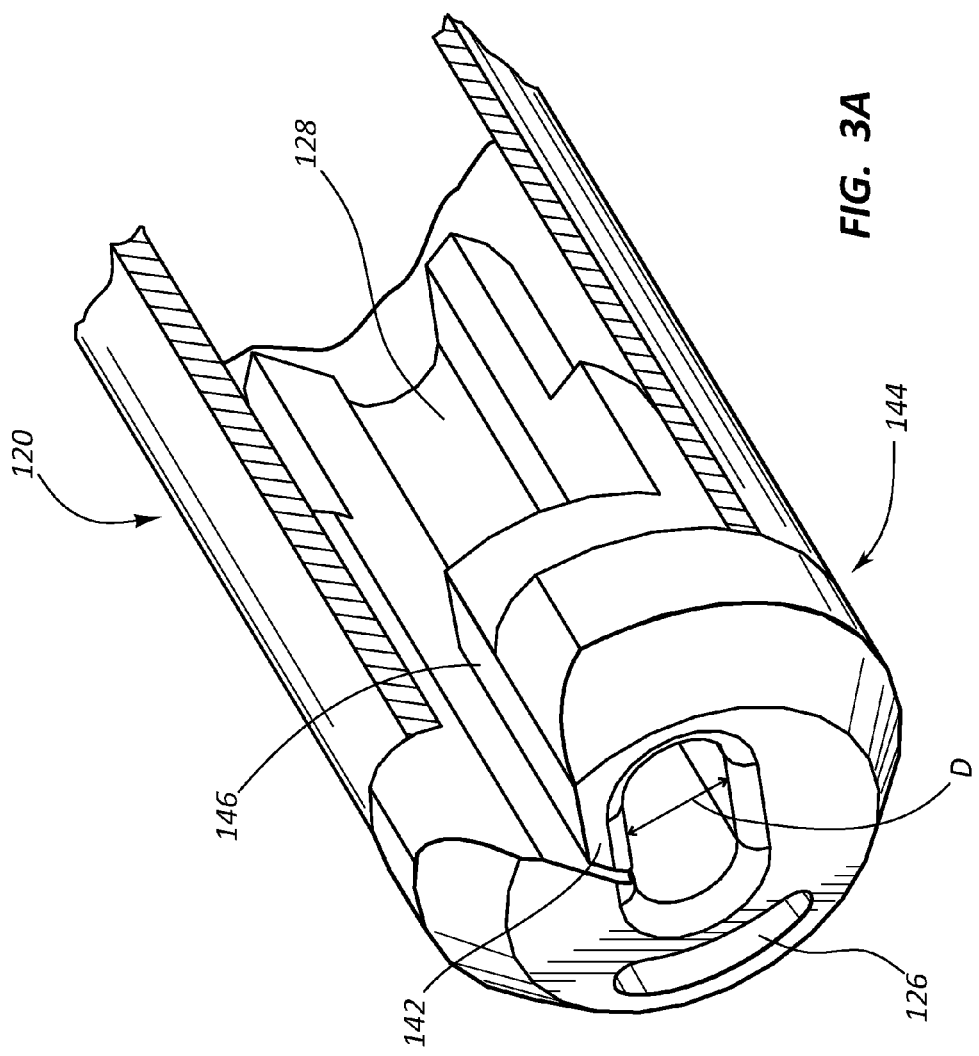
FIG. 3A is a close-up view of a distal end portion of another example sealant delivery device.

An alternative tip 144 is shown with reference to FIGS. 3A-3C. The tip 144 is mounted to a sealant shaft 120, which includes a sealant lumen 126 and an exchange lumen 128. The tip 144 includes a one-way door 142, which provides access into the exchange lumen 128. The tip 144 may include a taper 146 leading to the one-way door 142. The one-way door 142 may move from a closed position shown in FIG. 3B to an open position shown in FIG. 3C to permit passage of a suture into the exchange lumen 128. The one-way door 142 may automatically return back to the closed position shown in FIG. 3B upon removing the radially directed force applied to the one-way door 142 by the suture when inserting the suture into the exchange lumen 128.

The cantilever arm 42 and one-way door 142 described with reference to FIGS. 2A-3C are included as features of the tips 44, 144, respectively. In other examples, similar suture capturing or locking features may be integrated directly into the sealant shaft 20, 120, rather than being formed in a separate tip, which is inserted into an open distal end of the sealant shaft. In alternative configurations, additional features may be mounted on an exterior circumferential surface of the sealant shaft to assist in capturing the suture within the exchange lumen 128. In still further embodiments, the sealant shaft 20 includes the sealant lumen 26, but does not include a separate exchange lumen 28. The sealant shaft 20 may include a feature positioned on an outer surface thereof or at the distal tip thereof, which provides a slideable connection with the suture 62 for purposes of tracking the sealant delivery device along the suture 62 to the vessel puncture.

In other arrangements, the sealant shaft 20 does not include a side or lateral opening into the exchange lumen 28. The sealant shaft 20 may include a different rapid exchange feature for mounting the sealant delivery device 12 to the suture 62. The rapid exchange feature may make it possible to mount the sealant delivery device 12 to the suture 62 at a location spaced between the proximal and distal ends of the suture 62. The rapid exchange capability may be particularly useful when the suture is relatively long and flexible, making it difficult to thread the suture through the exchange lumen 28 and out of a proximal open end of the sealing shaft (e.g., along an entire length of the sealing shaft 20). In some arrangements, the rapid exchange feature includes an exchange lumen 28 open at its distal end 32 and then closed along at least a portion of its length to a location spaced proximal of the distal end opening 32 wherein a lateral opening is formed in the exchange lumen 28. The proximal end of the suture 62 may be threaded through the distal end opening 32 and out of the lateral opening at a location distal of the sealant manifold 22.

The sealant mixing device 24 may carry at least one sealant material. In one example, the sealant material carried by the sealant mixing device 24 includes at least two components that remain separated until just prior to delivering the sealant material to the vessel puncture. The sealant mixing device 24 is shown having a plunger 27 used to expel the sealant material from the sealant delivery device 12. Other structures and mechanisms may be used to mix, store, and eject the sealant material through the sealant shaft 20 to a tissue puncture. Example sealant mixing devices and related sealant materials are disclosed in U.S. patent application No. 61/692,859 filed on 24 Aug. 2012, and entitled "Sealant Storage, Preparation and Delivery Systems and Related Methods," and U.S. patent application No. 61/693,052, filed on 24 Aug. 2012, and entitled "Bioadhesive Mixing and Delivery Device and Methods", which patent applications are incorporated herein in their entireties by this reference.

Figure 4:
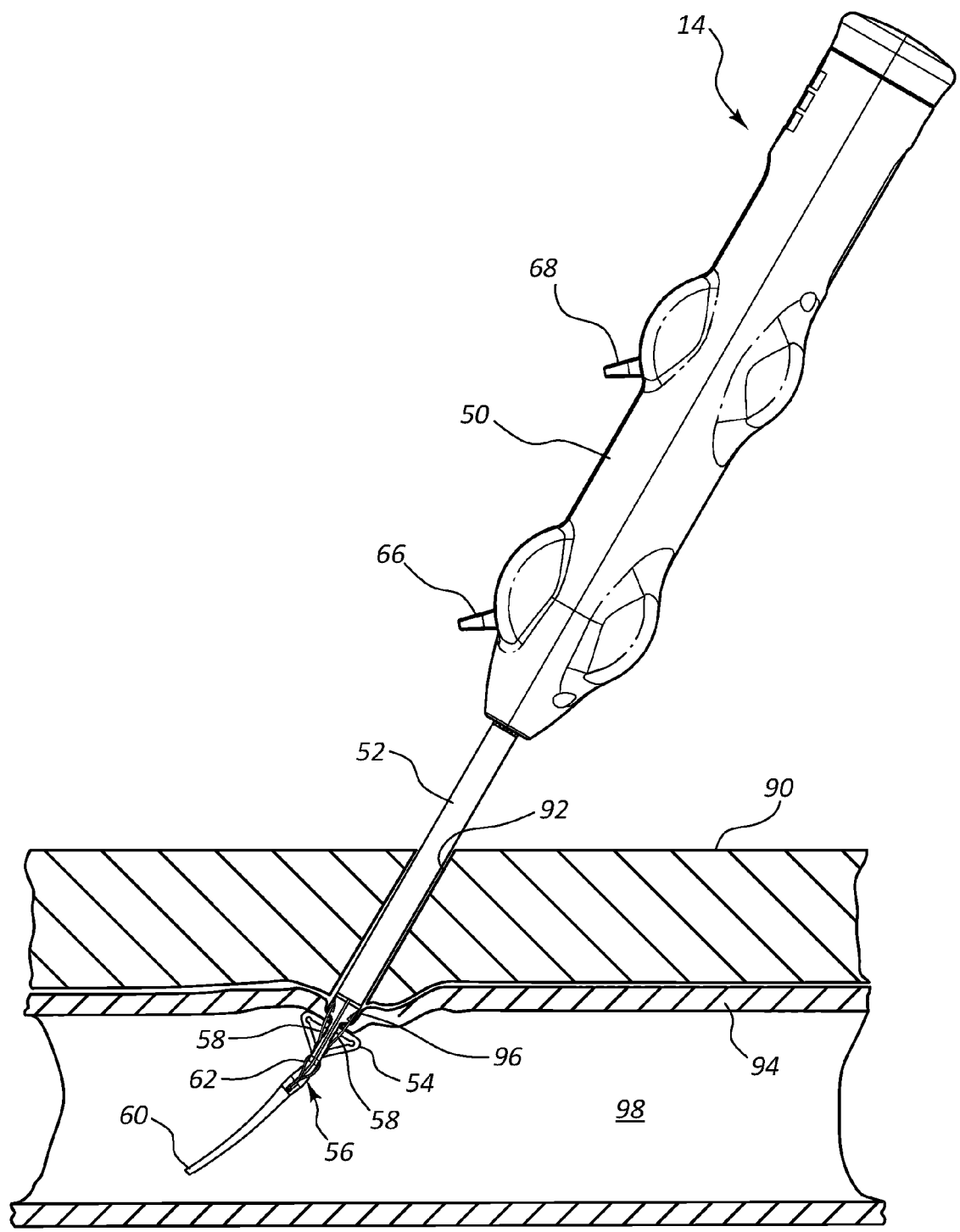
FIGS. 4-10 show steps of an example method of sealing a vessel puncture using the vascular closure system of FIG. 1.
Figure 5:
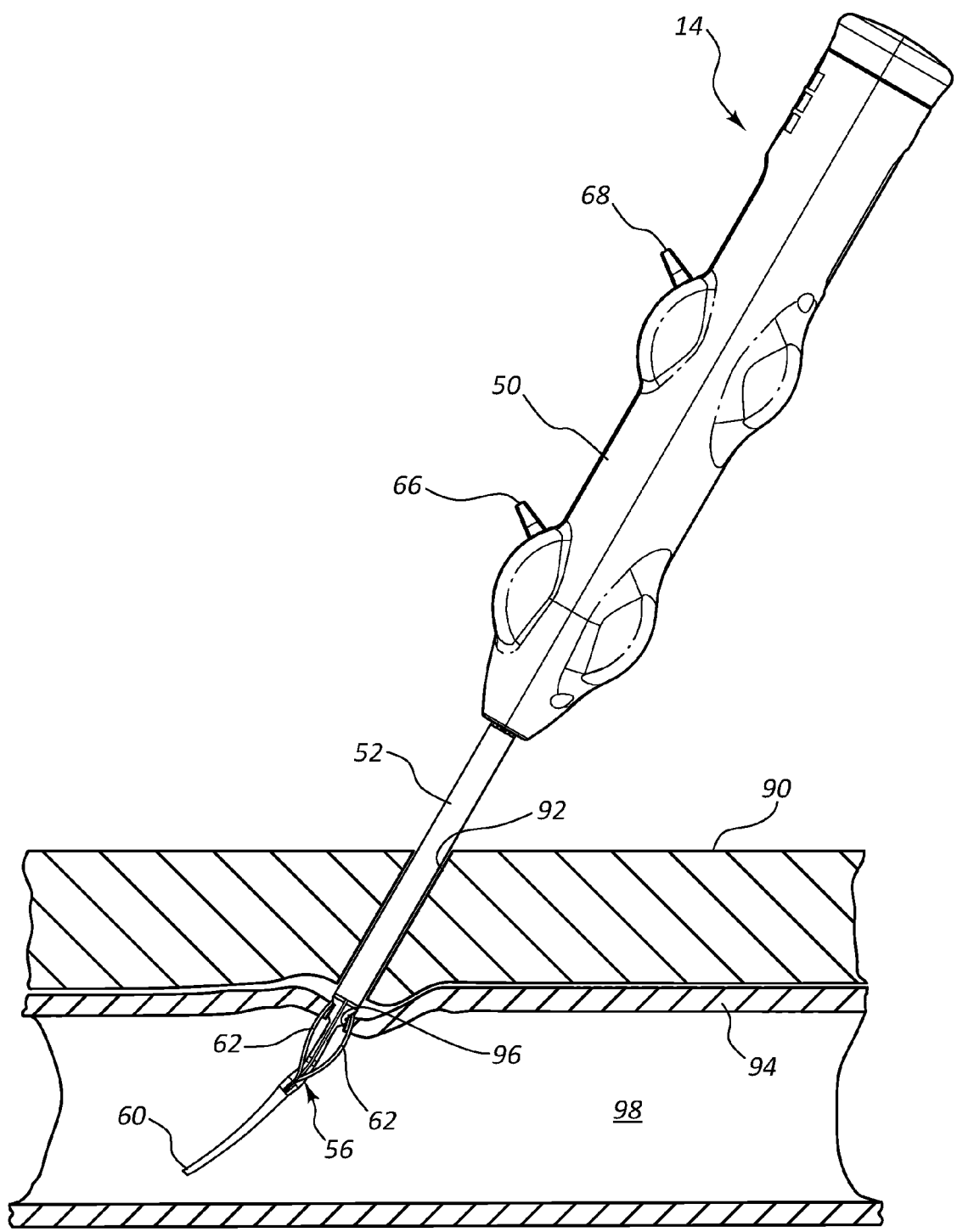
Figure 6:
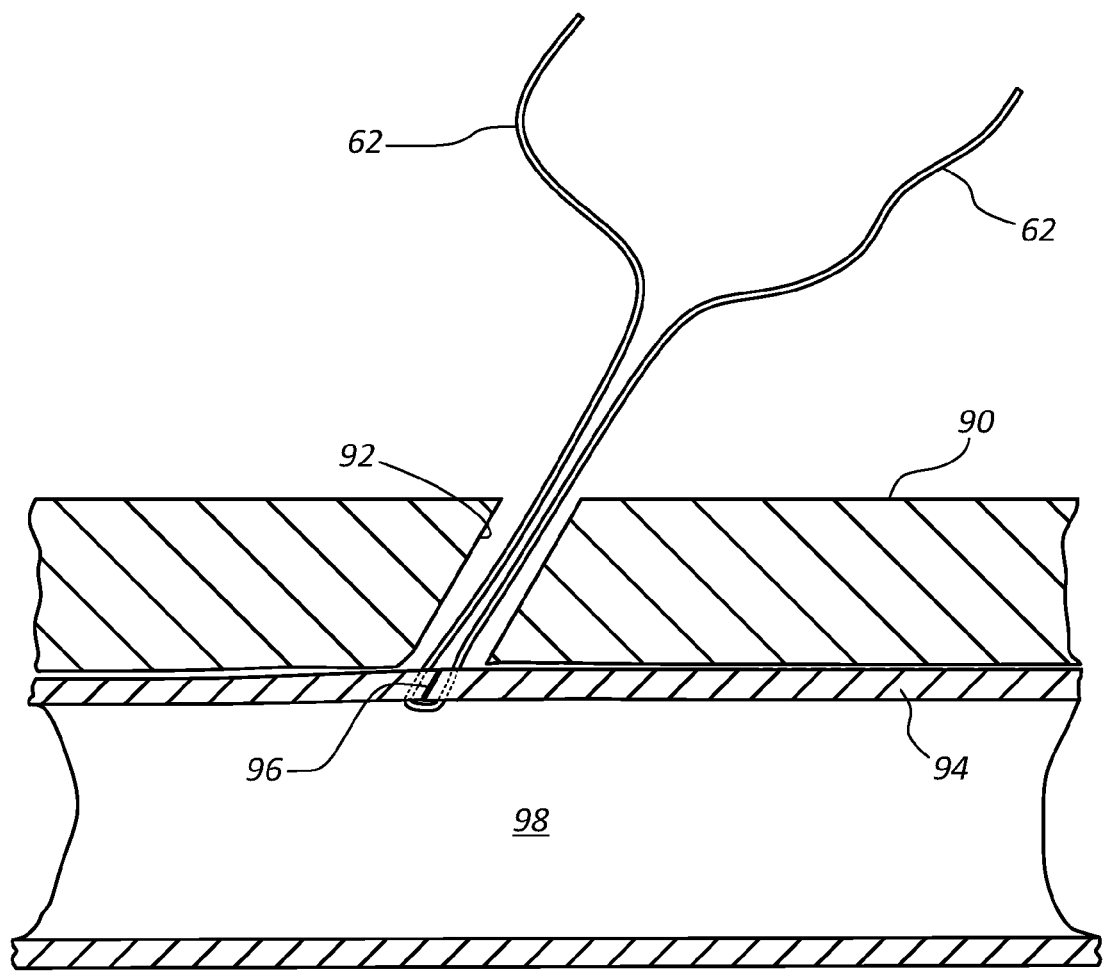
Figure 7:
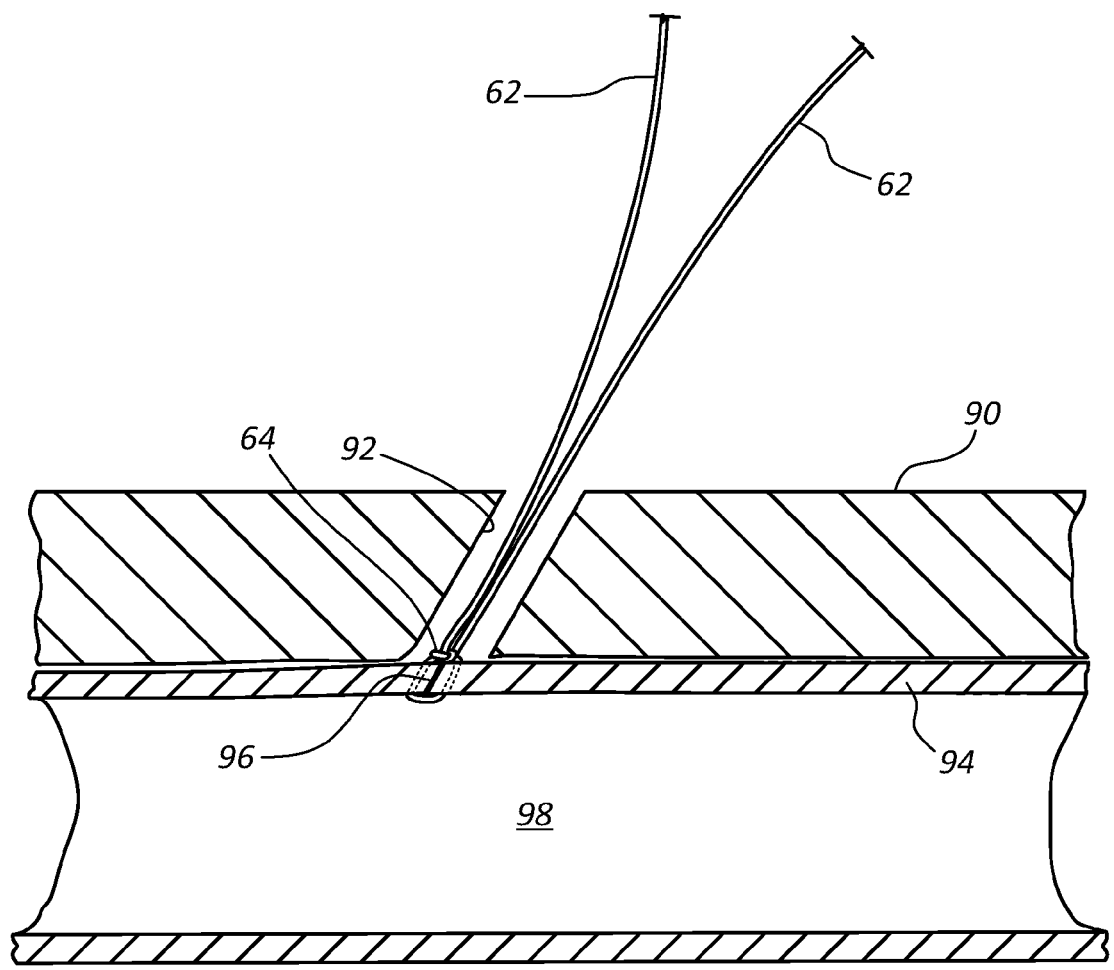

The suture placement device 14 shown in FIG. 1 includes a handle 50, and insertion shaft 52, an anchor 54, a suture carrying portion 56, a needle 58, and a distal locator tip 60. The handle 50 may include first and second actuators 66, 68. The suture carrying portion 56 may include a plurality of sutures 62. The suture placement device 14 may be operated to place at least one of the sutures 62 across a vessel puncture 96 as described below with reference to FIGS. 4-10. The first actuator 66 may be operated to move the anchor 54 into an expanded position to capture a vessel wall as shown in FIG. 4. The second actuator 68 may be operated to advance the needles 58 through the vessel wall and into contact with the suture carrying portion 56 to capture the suture 62. The second actuator may be operated in a reverse direction to retract the needles 58 to pull the suture 62 through the vessel wall. The first actuator 66 may be operated in a reverse direction to retract the anchor 54, followed by withdrawal of the suture placement device 14 from the vessel puncture. The suture 62 remains positioned extending through the vessel wall as shown in FIG. 6.

Details concerning operation of an example suture placement device are shown and described in U.S. patent application Ser. No. 13/490,816, filed on 7 Jun. 2012, and entitled "Large Bore Puncture Closure Device and Methods", which is incorporated herein in its entirety by this reference. Many types of suture placement devices may be used to position at least one suture across the vessel puncture. Typically, the suture placement device 14 is used to place at least one suture across the vessel puncture prior to other treatment and operational steps related to closing the vessel puncture. For example, the suture placement device 14 may be operated at shown in FIGS. 4-5 to place the sutures 62 across the vessel puncture prior to advancing the sealant delivery device 12 along the suture 62 to the vessel puncture.

Referring now to FIGS. 4-10, an example method of sealing a vessel puncture using the vascular closure system 10 is described in detail. Referring first to FIG. 4, at least one suture 62 is positioned across a vessel puncture 96 using suture placement device 14. The vessel puncture 96 is formed in vessel 94 and is accessible through a tissue tract 92 of a tissue layer 90.

The suture placement device 14 is advanced through the tissue layer 92 and the vessel puncture 96 to position the anchor 54, suture carrying portion 56, and distal locator tip 60 within the vessel lumen 98. The suture placement device 14 is then operated by actuating first actuator 66 to capture a wall of vessel 94 between a distal end surface of the insertion shaft 52 and proximal surfaces of the anchor 54. The second actuator 68 is then actuated to advance needles 58 through the wall of the vessel 94 and into contact with the sutures 62 carried by the suture carrying portion 56. The second actuator 68 is operated in a reverse direction to withdraw the needles 58 and sutures 62 through the vessel wall as shown in FIG. 5. The first actuator 66 is operated in a reverse direction to retract the anchor 54. The suture placement device 14 is then withdrawn from the vessel puncture 96 and tissue tract 92. The suture 62 remains extending across the vessel puncture 96 as shown in FIG. 6. Free ends of the suture 62 may extend out of the tissue layer 90 for handling by the operator.

The operator may tie a knot in at least one of the sutures 62 and advance the knot through the tissue tract 92 to the vessel puncture 96. The knot may be used to cinch at least one of the sutures 62 to maintain tension in the suture 62 to close the vessel puncture 96. At least one suture locking device may be used in combination with or in place of the knot 64 for maintaining tension in the suture 62 to hold closed the vessel puncture 96. The suture locking device (not shown) may be advanced along the suture 62 and into the tissue tract 92 to a position adjacent to the vessel puncture 96.

As discussed above, closing the vessel puncture 96 using only the sutures 62 and any knots or suture locking devices used therewith may provide an initial closure of the vessel puncture 96 (e.g., preliminary hemostasis). However, when closing relatively large vessel punctures such as vessel punctures in the range of about 10 F to 30 F (e.g., about 18 F to about 24 F), which are referred to as large bore vessel punctures, using sutures alone to close the vessel puncture may be inadequate to provide complete hemostatis. The sealant delivery device 12 may be used in combination with the suture closure shown in FIGS. 4-7 to further seal and maintain closure (e.g., hemostasis) of the vessel puncture 96.

Figure 8:
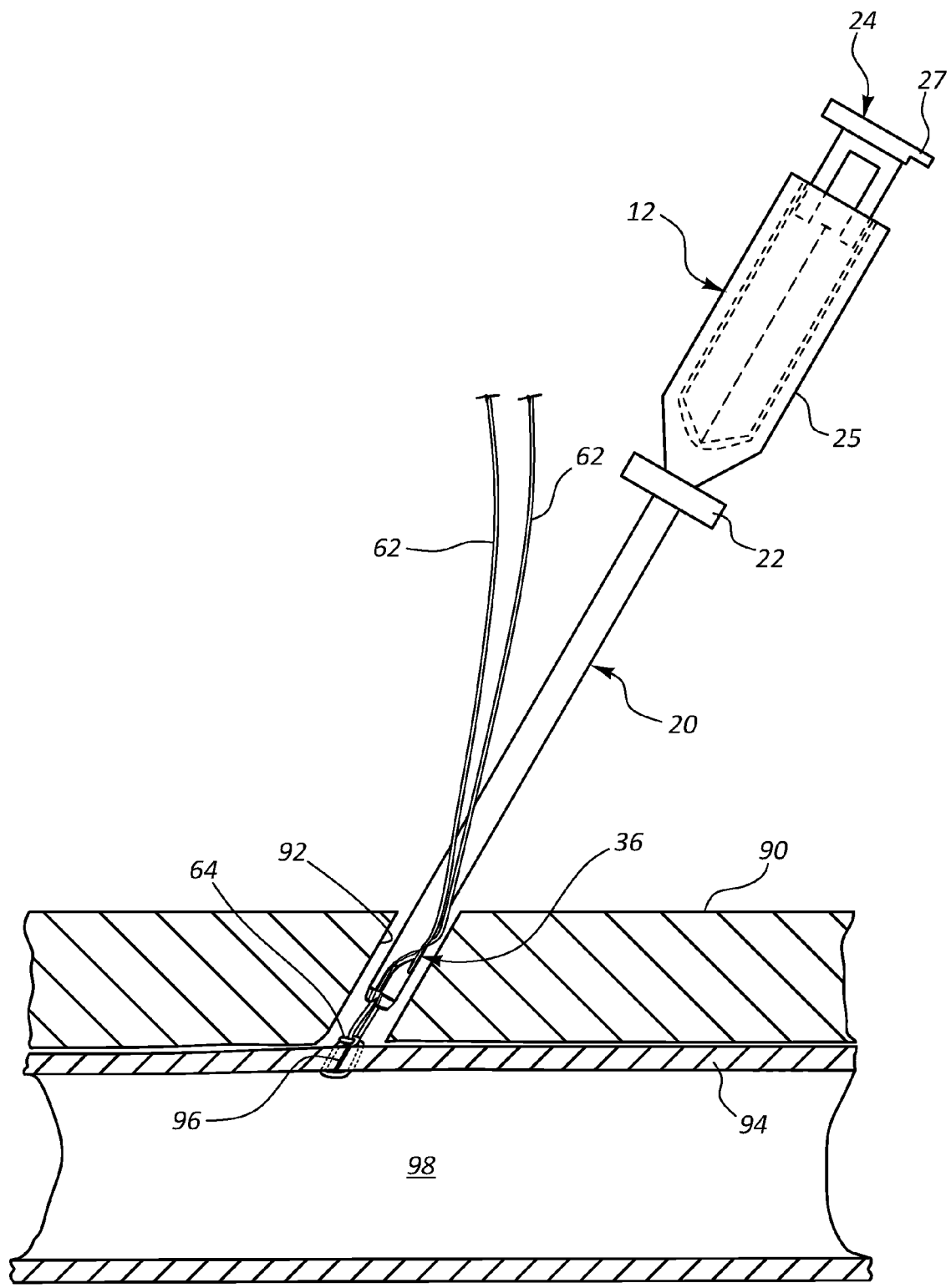

Referring to FIG. 8, the sealant delivery device 12 may be mounted to at least one of the sutures 62. In one example, the sutures 62 are positioned within the exchange lumen 28 and oriented within the longitudinal guide slot 36 as shown in FIG. 8. The sealant delivery device 12 is then advanced along the suture 62 to the vessel puncture 96. As mentioned above, there may be numerous ways to provide a connection between the sealant delivery device 12 and the suture 62 to assist in tracking or guiding the sealant delivery device 12 to the vessel puncture. The exchange lumen 28 shown in FIGS. 8 and 9 and described above is merely one example of a sealant shaft and associated tip construction that provides a positive connection between the sealant delivery device 12 and the sutures 62 while permitting relative sliding motion therebetween for guiding the sealant delivery device 12 along the sutures 62 to the vessel puncture. In one example, the sutures 62 maintain connection to the sealant shaft using a one-way door (e.g., via doors 42, 142 described above). In other examples, the sutures 62 are held in the sealant shaft by applying a rotation force to the sealant delivery device 12.

Figure 9:
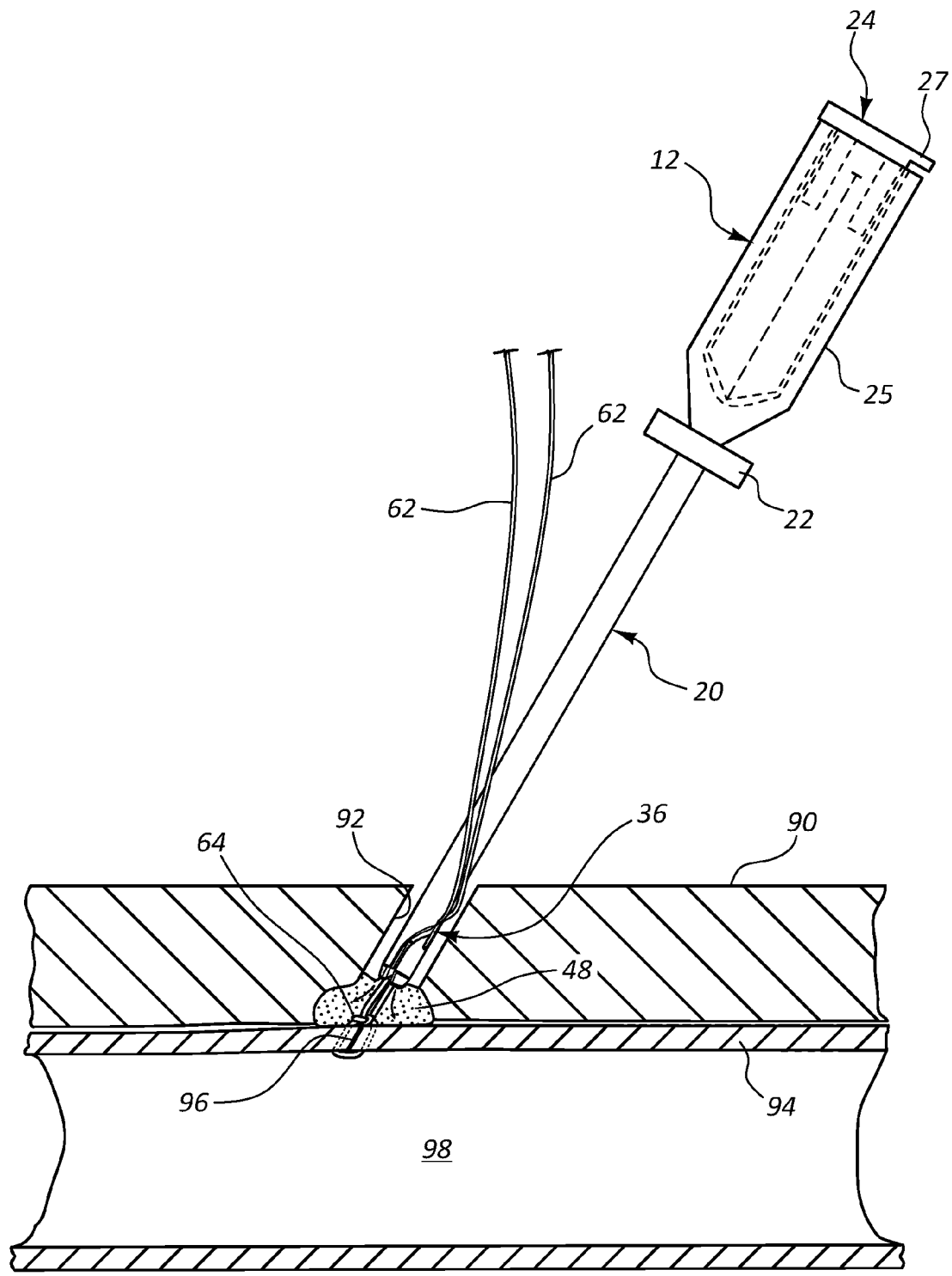

Referring to FIG. 9, the sealant delivery device 12 is operated to advance a volume of sealant through the sealant lumen 26 and into the area surrounding the vessel puncture 96 along an exterior of the vessel 94. The volume of sealant may form a sealant plug 48 that fills at least a portion of the tissue tract 92 and encapsulates at least a portion of the suture 62 and the knot 64. The plug 48 may provide further sealing of the vessel puncture 96. The plug 48 may bond with an outer surface of the vessel 94 adjacent to the vessel puncture 96. The plug 48 may also bond with the tissue layer 90 within the tissue tract 92. The plug 48 may bond directly to the suture 62 to provide a connection therebetween. The plug 48 may provide a secondary seal for the vessel puncture 96 and provide further hemostatis.

Figure 10:
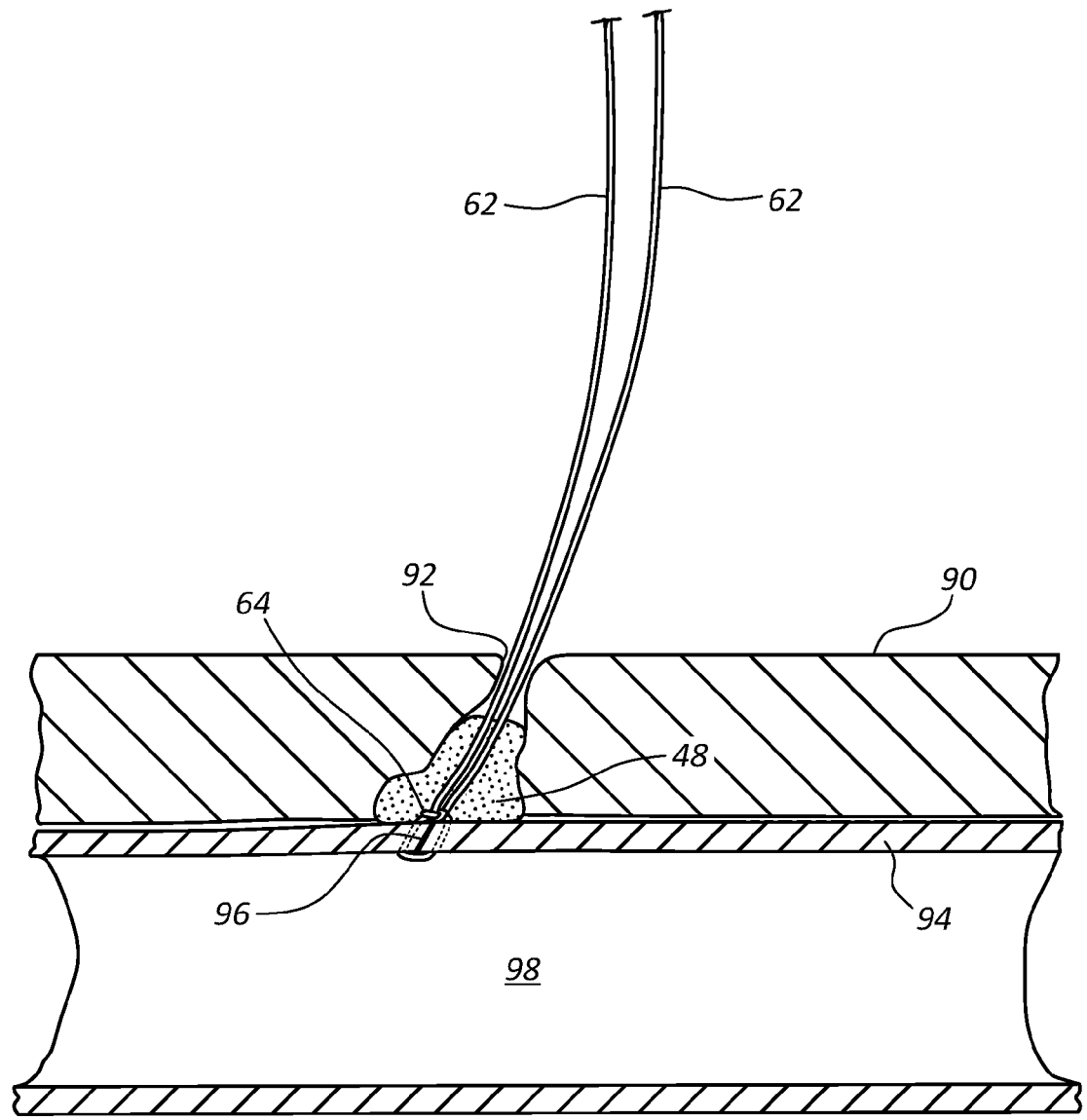

The sealant delivery device may then be withdrawn along the suture 62 and out of the tissue tract as shown in FIG. 10. The suture 62 may be trimmed to a shorter length. In at least one example, the suture 62 may be cut within the tissue tract 92 at a location below an outer surface of the tissue layer 90. The tissue tract 92 may close around the plug 48.

In other arrangements, a sealant shaft includes a sealant lumen and an exchange lumen that does not include a side opening. The exchange port may provide a rapid exchange mounting of the sealant delivery device to the sutures. The rapid exchange features may make it possible to mount the sealant delivery device to the sutures at a location spaced between proximal and distal ends of the sutures.

The sealant delivered by the vascular closure system 10 may be used in combination with or independent of at least partially sealing vessel puncture 96 with sutures 62 and corresponding suture knots 64 or a suture locking device. Using a combination of sutures and sealing material may be particularly effective in maintaining a sealed closure of a large bore vessel puncture, wherein sutures or sealing material independently may be less effective in maintaining closure of the vessel puncture.

The sealants discussed herein may comprise a single component, or may comprise multiple sealant components that are mixed together. The multiple sealant components may further react together to form a crosslinked network. The sealant components may be naturally derived or synthetic. Some example synthetic components include polyethers such as polyethylene glycol, polypropylene glycol and polytetrahydrofuran. Other examples of synthetic components may include polyamine compositions such as polyvinylpyrrolidones, polyethylene imines and hydrogenated polyacrylonitriles. Other example sealant components include polyacrylic and methacrylic compounds such as polyacrylic acid. Example naturally derived components include protienaceous compositions such as albumin, collagen and polylysine. Other examples include carbohydrate compositions such polyhyaluronic acid. The sealant components may also contain reactive functional groups to promote chemical crosslinking. The sealant components may be cross-linked by any known method including, for example, condensation reactions, Michael addition, and free radical. Functional groups used for crosslinking may include, for example, thiols, acrylates, amines, succinimydyls and aldehydes, to name a few. A particularly preferred bioadhesive comprises a two-part aldhehyde plus albumin composition. This composition may have the practical advance of not requiring pre-mixing, is gamma sterilizable, and provides high tissue adhesion.

In one example, the sealing material includes two separate components that remain separated from each other within the sealant mixing device 24 until delivery. In one example, the sealing material includes 20% solids in a 1:1 10 mL batch formulation. The first component includes 1.4 g of bovine serum albumin (BSA) and 3.6 mL of polyphenylene sulfide (PPS). The second component includes 25% glutaraldehyde in the amount of 2.6 mL and an additional 2.5 mL of deionized water. The amount of seeping material ejected at the vessel puncture may vary depending on, for example, the size of the vessel puncture. In one example, the total amount of bioadhesive material ejected is in the range of about 0.2 mL to about 1.0 mL, more preferably about 0.4 mL to about 0.6 mL.

The preceding description has been presented only to illustrate and describe exemplary embodiments of the invention. It is not intended to be exhaustive or to limit the invention to any precise form disclosed. Many modifications and variations are possible in light of the above teaching. It is intended that the scope of the invention be defined by the following claims.

What is claimed is:

1. A vascular closure assembly configured to seal a puncture in a vessel, comprising:
    a suture placement device operable to position at least one suture across the puncture to form a primary seal of the puncture;
    a sealant delivery device comprising a sealant delivery tube having a first lumen sized to receive the at least one suture, the sealant delivery device being slidable along the at least one suture to the puncture, and a second lumen configured to deliver a volume of sealant to the puncture after forming the primary seal to create a secondary seal of the puncture, wherein the sealant delivery tube comprises a helical shaped suture insertion slot at the distal end thereof.

2. The vascular closure assembly of claim 1, wherein the sealant delivery tube comprises a suture insertion slot at a distal end of the sealant delivery tube.

3. The vascular closure assembly of claim 1, wherein the sealant delivery tube comprises:
    a longitudinal guide slot open to the helical shaped suture insertion slot.

4. The vascular closure assembly of claim 1, wherein the sealant delivery tube comprises the helical shaped suture insertion slot at a distal end thereof, the insertion slot forms an acute angle.

5. The vascular closure assembly of claim 1, wherein the sealant delivery device comprises a suture retaining member positioned at a distal end thereof, the suture retaining member configured to permit one-way insertion of the at least one suture into the first lumen.

6. The vascular closure assembly of claim 1, wherein the suture placement device positions the at least one suture on opposite sides of the puncture, and tension is retained in the at least one suture with one of a knot and a suture locking device to at least partially seal the puncture prior to delivering the volume of sealant.

7. A method of closing a puncture in a vessel, comprising:
    providing a suture placement device and a sealant delivery device;
    positioning at least one suture across the puncture with the suture placement device;
    sealing the puncture with the at least one suture;
    advancing the sealant delivery device along the at least one suture to the puncture;
    delivering a volume of sealant through the sealant delivery device to the puncture to further seal the puncture, wherein the sealant delivery device comprises a helical shaped suture insertion slot at the distal end thereof.

8. The method of claim 7, further comprising providing a releasable connection between the sealant delivery device and the at least one suture.

9. The method of claim 7, wherein delivering a volume of sealant includes mixing the volume of sealant in the sealant delivery device during delivery.

10. The method of claim 7, wherein the sealant delivery device comprises a first lumen configured to receive the at least one suture and a second lumen configured to deliver the volume of sealant.

11. The method of claim 7, wherein sealing the puncture comprises advancing a knot along the at least one suture to the puncture.

12. The method of claim 7, wherein the at least one suture comprises two suture portions and the sealant delivery device is advanced along both suture portions to the puncture.

13. The method of claim 7, wherein the sealant delivery device comprises a sealant shaft and the helical shaped suture insertion slot extending proximally from an open distal end of the sealant shaft, the method comprising inserting the at least one suture into the insertion slot prior to advancing the sealant delivery device.

14. The method of claim 13, wherein the sealant delivery device comprises a guide slot spaced proximal of the open distal end and intersecting with the helical shaped suture insertion slot, the method comprising inserting the at least one suture through the insertion slot and into the guide slot prior to advancing the sealant delivery device.

15. The method of claim 7, further comprising inserting the at least one suture into a portion of the sealant delivery device before advancing the sealant delivery device.

16. A method of sealing a puncture in a vessel accessible through a percutaneous incision, the method comprising:

providing a sealant delivery device having first and second lumens, and a suture placement device;

positioning at least one suture across the puncture with the suture placement device;

advancing a knot along the at least one suture to seal the puncture;

positioning the at least one suture in the first lumen;

advancing the sealant delivery device along the at least one suture to the puncture;

delivering a volume of sealant through the second lumen to the puncture to seal the puncture, wherein the sealant delivery device comprises a helical shaped suture insertion slot at the distal end thereof.

17. The method of claim 16, the helical shaped suture insertion slot providing lateral access into the first lumen, and positioning the at least one suture in the first lumen includes laterally inserting the at least one suture through the helical shaped suture insertion slot.

18. The method of claim 17, wherein the sealant delivery device includes a guide slot intersecting the helical shaped suture insertion slot and extending longitudinally, and positioning the at least one suture in the first lumen includes positioning the at least one suture in the guide slot.

19. The method of claim 16, wherein the sealant comprises a resorbable bioadhesive.

20. The method of claim 16, wherein positioning at least one suture across the puncture with the suture placement device includes inserting the suture placement device in the puncture, advancing at least one needle through a wall of the vessel adjacent to the puncture, drawing the at least one suture through the wall of the vessel, and removing the suture placement device from the puncture.

* * * * *